United States Patent [19]

Maurer et al.

[11] 4,019,518
[45] Apr. 26, 1977

[54] ELECTRICAL STIMULATION SYSTEM

[75] Inventors: Donald D. Maurer, Anoka; Paul D. Sorenson, Blaine, both of Minn.

[73] Assignee: Medtronic, Inc., Minneapolis, Minn.

[22] Filed: Aug. 11, 1975

[21] Appl. No.: 603,434

[52] U.S. Cl. .............................. 128/419 R; 128/404
[51] Int. Cl.² .......................................... A61N 1/34
[58] Field of Search ........... 128/404, 419 E, 419 R, 128/421, 422, 423

[56] References Cited

UNITED STATES PATENTS

| 3,646,940 | 3/1972 | Timm et al. | 128/421 |
| 3,805,796 | 4/1974 | Terry, Jr. et al. | 128/421 |
| 3,833,005 | 9/1974 | Wingrove | 128/422 |
| 3,888,261 | 6/1975 | Maurer | 128/421 |

*Primary Examiner*—William E. Kamm
*Attorney, Agent, or Firm*—Lindquist & Vennum

[57] ABSTRACT

An electrical stimulation system for selectively stimulating portions of the body. The system includes an external device for alternately transmitting stimulus signals and control signals to an implantable receiver. The receiver includes a plurality of output devies adapted to apply the stimulus signals to the body and circuitry for routing the stimulus signal to the output devices under the control of the control signals. In a preferred embodiment, the control signals are formed of an alterably preselected number of pulse signals with the routing circuitry routing each of the stimulus signals to the output devices in predetermined correspondance with the number of pulse signals within a different one of the control signals. The system of the present invention may be employed to sequentially stimulate several stimulation sites, with the stimulation sites being selected to combat the same or different body disfunctions. Alternatively, the system of the present invention may be employed to repetitively stimulate the same stimulation sites while allowing an alteration in the stimulation sites to combat nerve fatigue or to provide a more effective electrode configuration, for example.

34 Claims, 2 Drawing Figures

ELECTRICAL STIMULATION SYSTEM

BACKGROUND OF THE INVENTION

The electrical stimulation of various biological systems is known to the prior art. For example, pain suppression by electrical nerve stimulation is an accepted technique. Motor control through selective nerve and/or muscle stimulation has also been usefully employed. More recent developments include electrical treatment of spinal curvature and brain stimulation for various purposes including thalamic stimulation for pain suppression and cerebellum stimulation for the treatment of epilepsy and for motor control.

In each of the above mentioned electrical stimulation applications, the value of alternative electrode configurations is readily apparent. For example, in many direct nerve stimulation applications the nerves to be stimulated are sheathed with other nerve bundles, or bundle branches. Thus, to optimize the desired stimulation of a specific nerve bundle it is necessary to provide a specific orientation of the electrode or electrodes relative to the several nerve bundles. It has also been established that an electrode may migrate, either longitudinally or by rotating around the nerve bundles, thus requiring a reorientation of the electrodes relative to the nerve.

Within other environments, the optimization of the electrode configuration may be impossible, or nearly so, for some time after placement of the electrodes. For example, the effects of cerebellum stimulation are often delayed for several weeks after the implant. In this situation, it is impossible, at the time of implant, to accomplish anything more than the positioning of a plurality of electrodes with the optimization of the electrodes through which the stimulation is to occur being delayed. Thus, a system by which electrodes can be positioned, and later selected, is desirable for these and many other stimulation applications. In other instances, it may be desirable to stimulate various biological systems with a single implanted receiver by sequentially selecting differing electrode configurations. For example, a spinal curvature having two treatable curves may be treated through the implantation of a single stimulator with the output of that stimulator being sequentially alternated between the electrodes to treat each of the curves. Other multiple treatment situations may similarly be accomplished with a stimulator having the ability to sequentially select differing electrode configurations.

In addition to the above, it is also known that changing the location of the sites at which the stimulation energy is applied can reduce the fatigue, nerve fatigue, for example, commonly attending a repetitive stimulation at the same site or sites.

Electrodes having multiple leads and electrode contacts have been developed for altering the electrode configuration, an example being illustrated in U.S. Pat. No. 3,738,368, issued June 12, 1973. With this electrode, selective nerve bundle stimulation is accomplished by coupling less than all of the leads to a source of stimulation energy. The lead selection may be altered until the optimal combination is found. Within the system disclosed in the referenced patent, it is contemplated that the electrode will be positioned on the nerve and the leads brought out through the skin for temporary connection to a suitable source of stimulation energy. After several days of stimulation utilizing different combinations of leads, the most effective electrode configuration is determined and the unnecessary leads are severed.

Other systems have been proposed in which alternate output paths may be selected through the application of an external signal. For example, in U.S. Pat. No. 3,311,111 the use of bistable magnetic reed switches is proposed for the control of several stimulator functions including, pulse rate, voltage, current or duration as well as the selection of alternative output paths or leads. Within this system, a magnetic field is applied to effect the desired alteration with that alteration remaining effective until the reapplication of the magnet field. Of course, the system is susceptible to a "switching" by an extraneous magnetic field.

Another system in which the output path is selected in accordance with an external signal is disclosed in application Ser. No. 422,896, filed Dec. 7, 1973, now U.S. Pat. No. 3,888,261 which is commonly owned with the present application and which is hereby incorporated by reference. Within this system, alternating stimulus and control signals are transmitted to an implanted receiver with the receiver switching the stimulus signals between the outputs under the control of the control signals. The outputs each include independent channels with the receiver switching from channel to channel on the occurrence of a control signal.

SUMMARY OF THE PRESENT INVENTION

The present invention provides an electrical stimulation system capable of selectively stimulating portions of the body. An external transmitter alternately transmits stimulus signals and control signals to an implantable receiver. The receiver includes a plurality of output devices adapted to apply the stimulus signals to the body and includes circuitry responsive to the control signals for selectively routing stimulus signals to the output devices. In a preferred embodiment, the control signals include at least one pulse signal with the number of pulse signals occurring between stimulus signals being alterable. The routing circuitry includes components responsive to the number of pulse signals in each control signal for selectively routing each stimulus signal to a predetermined output device configuration in predetermined correspondence with the number of pulse signals within a different one of the control signals.

The system of the present invention selects an output device configuration for each stimulus signal which allows a sequential application of the stimulus signals to varying output configurations or, alternatively, a periodic alteration in output configurations. Thus, the stimulator of the present invention allows an initial optimization of the electrode configuration, a later alteration or reoptimization of that configuration or a periodic alteration in the output device configuration in a manner which may be used in any of the biological system stimulation environments discussed above. Other biological systems to which the stimulator of the present invention can be usefully applied will be immediately apparent to those familiar with the art. Also, inasmuch as the routing of each stimulus signal is independently established, any effects of extraneous noise will be automatically corrected on the next succeeding control pulse.

DETAILED DESCRIPTION OF THE DRAWINGS

Figure 1:
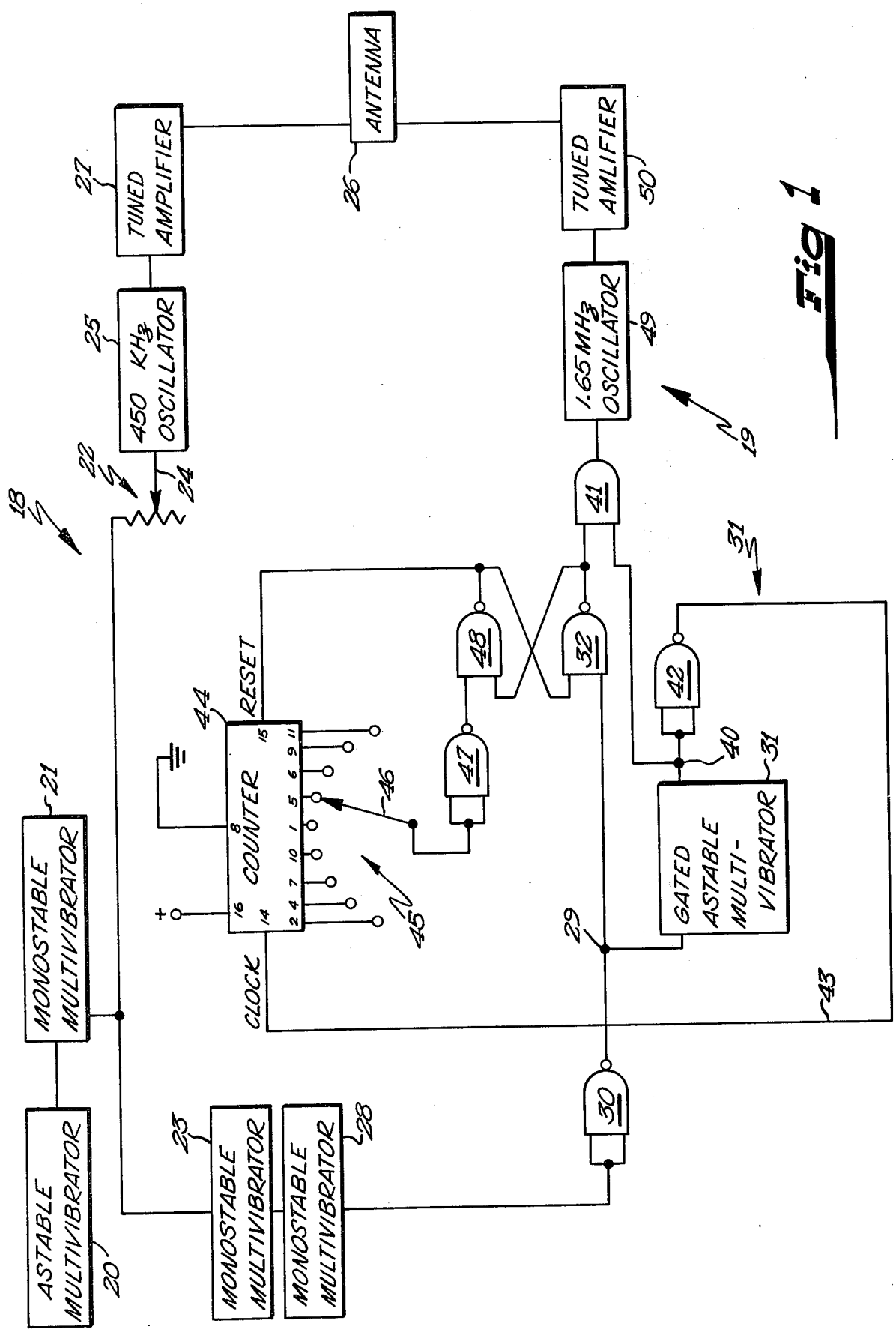
FIG. 1 illustrates a transmitter forming a portion of a preferred embodiment of the present invention.

Throughout the drawings, reference numerals 1-16 represent pin designations as established by the manufacturers of the several components with which they appear or are described.

With reference to FIG. 1, there is shown a transmitter forming a portion of a preferred embodiment of the stimulator of the present invention, the transmitter having a stimulus signal path 18 and a control signal path 19. An astable multivibrator 20 has its output connected to a monostable multivibrator 21, the monostable multivibrator 21 being triggered on the trailing edge of each pulse from the astable multivibrator 20. The output of the monostable multivibrator 21 is applied to an oscillator 25 in the stimulus signal channel 18 and to a second monostable multivibrator 23 in the control signal channel 19. The output of oscillator 25 is amplified by a tuned amplifier 27 and applied to antenna 26. Control of the stimulus amplitude is achieved in the tuned amplifier 27 by the variable resistor 22.

The monostable multivibrator 23 is triggered on the trailing edge of the signal from the monostable multivibrator 21 and has its output applied to a monostable multivibrator 28. The monstable multivibrator 28 is triggered on the trailing edge of the signal from the monostable multivibrator 23 and has its output connected to a junction 29 through an inverter formed by NAND gate 30. The junction 29 is connected in controlling relation to a gated astable multivibrator 31 and as one input to NAND gate 32.

The output of gated astable multivibrator 31 is connected, through junction 40, as one input to the AND gate 41 and is inverted by NAND gate 42 and applied to the clock terminal of a counter 44 via line 43. The counter 44 is of the type known as a Johnson Counter having decoded outputs and the pins 2, 4, 7, 10, 1, 5, 6, 9 and 11, which represent counter states 1-9, respectively, are each connected to a different contact of a rotary switch 45 having a movable selector arm 46. When the state of the counter advances under control of clock pulses appearing on the line 43, the output terminals of the counter 44 will sequentially go HIGH (positive logic) with one clock pulse applying a HIGH to pin 2, two clock pulses applying a HIGH to pin 4 and so forth, sequentially, for the remainder of the pins 7, 10, 1, 5, 6, 9 and 11. The signal appearing at the pin whose contact is in electrical communication with the selector arm 46 will be applied through an inverter formed of NAND gate 47 as one input to NAND gate 48. NAND gates 32 and 48 form a latch, in known manner, with the output of NAND gate 48 being applied as a reset signal to counter 44 and the output of NAND gate 32 being applied as the other input to AND gate 41. The output of AND gate 41 is applied to the antenna 26 through an oscillator 49 and tuned amplifier 50.

In operation, the astable multivibrator 20 will apply output pulses at the desired stimulation frequency with the monostable multivibrator 21 providing an output signal on the occurrence of each output from the astable multi-vibrator 20. The monostable multivibrator 21 establishes the width of the pulses in the stimulus channel 18 while the amplitude of those pulses is controlled through the variable resistor 22, the resulting pulse being transmitted as a stimulus signal by antenna 26, in known manner. The oscillator 25 may be selected to provide a carrier frequency of 450KHz.

When the junction 29 is LOW, the multivibrator 31 is gated off or disabled and the junction 40 is held HIGH. Thus, with the junction 29 LOW, the AND gate 41 has at least one HIGH input and there are no clock pulses applied to the clock pulse input terminal of counter 44. The monostable multivibrator 23 will provide an output pulse on the trailing edge of each output pulse from monostable multivibrator 21 while the monostable multivibrator 28 will produce an output pulse on the trailing edge of each output pulse from the monostable multivibrator 23. As will be appreciated from the following discussion, the duration of the pulse from the monostable multivibrator 23 establishes an interval by which the first signal generated in control signal channel 19 follows each signal appearing in stimulus signal channel 18.

On the triggering of monostable multivibrator 28, its output will go HIGH and be inverted by a NAND gate 30 to apply a LOW at the junction 29. A LOW at the junction 29 will result in the junction 40 going HIGH and the output of NAND gate 32 going HIGH producing two HIGH inputs to AND gate 41, and a HIGH output from AND gate 41, for the duration of the pulse from the monostable multivibrator 28. This HIGH output from AND gate 41 will result in the transmitting of a signal via antenna 26 through operation of the oscillator 49 and tuned amplifier 50, in known manner. On completion of its output pulse, the output of monostable multivibrator 28 will go low and result in a HIGH at the junction 29. The HIGH at the junction 29 will cause the oscillator 31 to begin running to apply clock pulses to the counter 44 via the line 43.

The HIGH appearing at the junction 29 after completion of the output pulse from monostable multivibrator 28 will not alter the HIGH output of NAND gate 32. Thus, AND gate 41 continues to have one HIGH input. With the oscillator 31 running, the junction 40 will alternate between HIGH and LOW states causing the AND gate 41 to have an alternating HIGH and LOW output, antenna 26 transmitting a radio frequency signal whenever the output of AND gate 41 is HIGH. The frequency of the oscillator 31 is selected such that the transmitted signals resulting from its oscillation are shorter in duration than the pulses from the monostable multivibrator 28.

With the oscillator 31 running, line 43 will apply clock pulses to the counter 44. On the occurrence of each pulse, the counter 44 advances its state. When the state of the counter advances to the pin with which the selector arm 46 is in contact, a HIGH signal will be applied to the selector arm 46, be inverted by the NAND gate 47 and be applied as a LOW to one input of NAND gate 48. Upon the one input of NAND gate 48 going LOW, the output of NAND gate 48 will go HIGH and reset the counter 44 while driving the output of the NAND gate 32 LOW to disable the AND gate 41 and thereafter prevent its ouput from going HIGH. Thus, with junction 29 LOW, the operation of the oscillator 31 causes one input of the AND gate 41 to alternately switch between HIGH and LOW states to provide a series of transmitted signals while the counter controls the state of the other input of AND gate 41 and the number of such signals transmitted. Of course, with the selector arm 46 set to provide nine transmitted signals, the total number of signals transmitted will be ten inasmuch as a first signal results from the triggering of the monostable multivibrator 28, the duration of the signal from the monostable multivibrator 28 being longer than those resulting from the running of the oscillator 31. In addition, the total cumulative time of the output pulses from the monostable multivibrators 21, 23 and 28, plus the time necessary to produce the maximum number of signals under the control of the counter 44, is less than the period of the astable multivibrator 20 such that signals from each channel will alternate with each other at the antenna 26. That is, by viewing each signal resulting from the triggering of monostable multivibrator 28 and the following signals generated under the control of the counter 44 as a single control signal, the stimulus signals and control signals will alternate in time and be alternately transmitted by the antenna 26.

Figure 2:
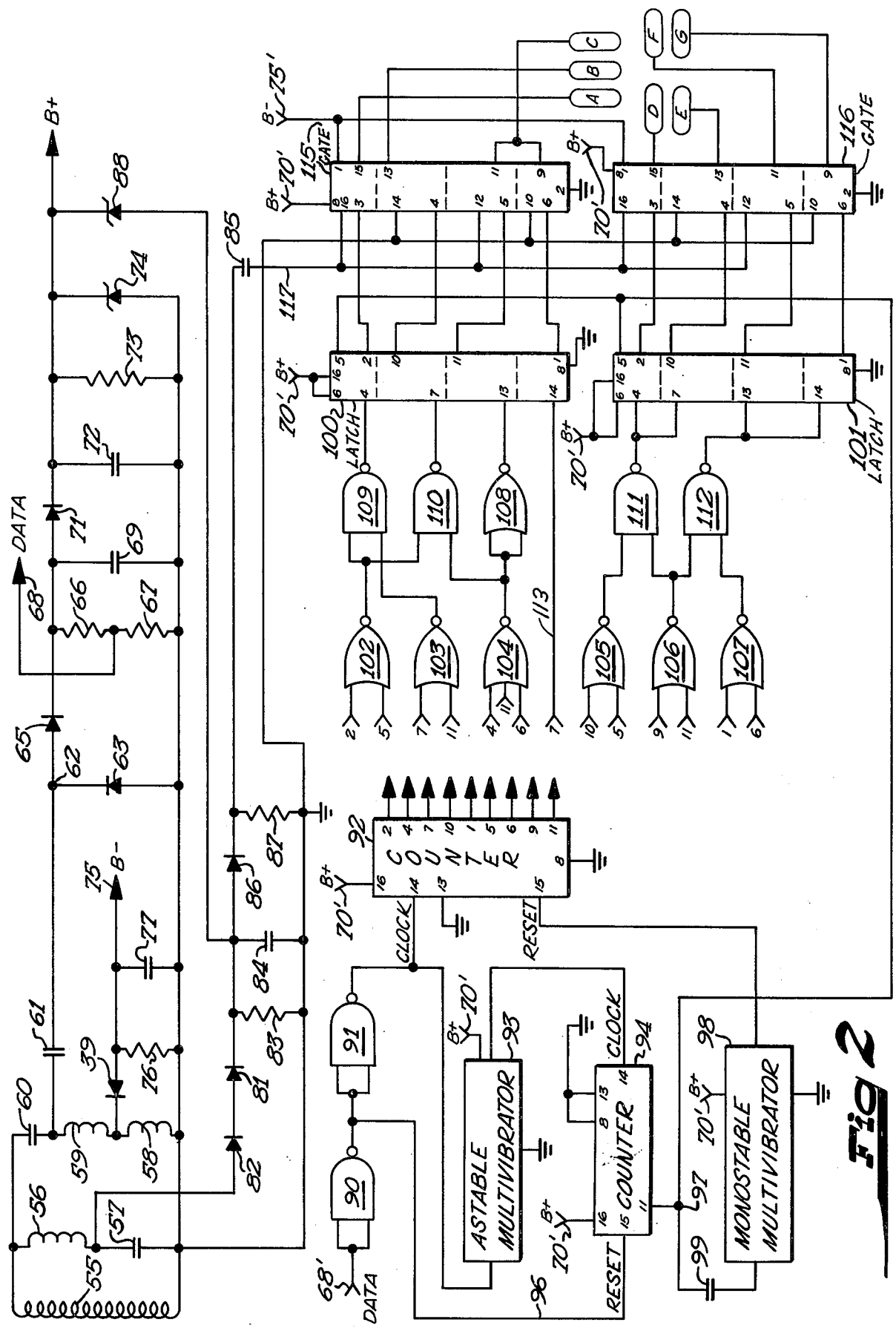
FIG. 2 illustrates a receiver forming a portion of a preferred embodiment of the present invention.

Referring now to FIG. 2, there is shown a preferred receiver embodiment forming a part of the present invention. An antenna 55 is parallel connected with a first reactive voltage divider, formed of inductance 56 and capacitance 57, and a second reactive voltage divider, formed of inductances 58 and 59 and capacitance 60. The inductance 56 and capacitance 57 are selected to resonate with the antenna 55 at one of the carrier frequencies of the transmitter of FIG. 1, 450KHz in this instance, for example. Inductances 58 and 59 and capacitance 60 are similarly selected to resonate with the antenna 55 at the second carrier frequency of the transmitter of FIG. 1, 1.65MHz in this instance, for example. Through their ability to resonate with the antenna 55 at different frequencies, the reactive voltage dividers illustrated in FIG. 2 form a passive frequency discriminator of the type described in application Ser. No. 422,897, filed Dec. 7, 1973, now Pat. No. 3,893,463 which is commonly owned with the present application and which is hereby incorporated by reference.

The junction intermediate inductance 59 and capacitor 60 is connected to one plate of capacitor 61 while the other plate of capacitor 61 is connected to a junction 62. The junction 62 is connected to ground through a diode 63 and to a junction 64 through a diode 65. Junction 64 is connected to ground through a voltage divider formed of resistances 66 and 67 with junction intermediate resistances 66 and 67 being connected to a terminal 68. The junction 64 is also connected to ground through a resistance 69 and to a terminal 70 through a diode 71. The terminal 70 is connected to ground through a capacitor 72, resistance 73 and zener diode 74.

The junction intermediate the inductances 58 and 59 is connected via diode 39 to a terminal 75 and to ground through a resistance 76 and a capacitor 77. The junction intermediate the capacitance 57 and inductance 56 is connected to a junction 80 through diode 81 and 82 and the junction 80 is connected to ground through a resistance 83 and capacitance 84 and to an output capacitor 85 through a diode 86. A resistor 87 connects the junction intermediate the capacitor 85 and the diode 86 to ground while the junction 80 is connected to the terminal 70 through a diode 88.

The first transmitted control signal pulse signal resulting from the triggering of monostable multivibrator 28 results in a pulse signal at the terminal 68 and the creation of a positive voltage supply at the terminal 70. Since the pulse signal resulting from the triggering of monostable multivibrator 28 is longer than the succeeding pulse signals forming the control signal, it makes the major contribution to the positive supply voltage at the terminal 70. Similarly, the signals appearing at the terminal 68 from the successive pulse signals are shorter than the initial pulse signal. However, all of the pulse signals contribute to the maintenance of the positive supply voltage at the terminal 70. Also, each of the pulse signals forming the control signal received at the antenna 55 result in the creation and maintenance of a negative supply voltage at the terminal 75. Similarly, each stimulus signal received at the antenna 55 results in the application of a stimulation pulse to the capacitor 85 with the resistor 87 allowing a biphasic stimulation, as is well known to those familiar with the art. The signals appearing at the terminals 68, 70 and 75 are applied to the primed terminals of like reference number in FIG. 2. For example, the signals at the terminal 68 are applied at the terminal 68'.

Terminal 68' is connected to an inverter formed by NAND gate 90 with the output of NAND gate 90 being again inverted by NAND gate 91 and applied as a clock pulse input to a counter 92 and as an enable input in astable multivibrator 93. Output pulses from astable multivibrator 93 are applied as clock inputs to the counter 94 via a line 95 while the reset terminal counter 94 is connected intermediate the NAND gates 90 and 91 via line 96.

One output terminal of counter 94 is connected to a junction 97, the selected terminal determining the amount of time between the initiating of operation of the astable multivibrator 93 and the appearance of signal at the terminal 97. For example, if the terminal 97 is connected to the terminal of counter 94 representing the state or count of 2, the terminal 97 will go HIGH in response to the second clock pulse applied to the counter 94 over the line 95. In practice, the counter 94 is a decade counter and the junction 97 may be connected to the terminal representative of a counter state or count of 10. The junction 97 is connected to a monostable multivibrator 98, through a coupling capacitor 99, and to the set input terminals of latches 100 and 101. A HIGH appearing at the set input terminal of the latches 100 and 101 causes the latches to apply to their output terminals that signal then appearing at their input terminals. The latches 100 and 101 each contain four independent functional sections represented by the phantom lines. The output of the monostable multivibrator 98 is applied to the reset terminal of the counter 92, the counter 92 being reset on the leading edge of the signal from the monostable multivibrator 98.

Logic circuitry composed of NOR gates 102 -108, NAND gates 109–112 and line 113 have their inputs connected to the outputs of the counter 92 and their outputs connected to the inputs of the latches 100 and 101. The numerals appearing at the inputs of the NOR gates 102–107 are those of the pins of the counter 92 to which they are connected. The line 113 is connected to the pin 7 of counter 92.

The outputs of the latches 100 and 101 are connected as enable signals to transmission gates 115 and 116. As was the case with the latches 100 and 101, each of the transmission gates 115 and 116 have four functionally independent sections indicated in phantom in FIG. 2. The output capacitor 85 is connected to a line 117 and the line 117, and its associated group line 118, are connected to alternate functional sections of the transmission gates 115 and 116. The outputs of the transmission gates 115 and 116 are connected to electrodes A through G.

In operation, signals appearing at the terminal 68 are applied at the terminal 68' and inverted by the NAND gate 90. A signal appearing at the terminal 68' thus results in a LOW on the line 96 to remove the reset signal to the counter 94. The NAND gate 91 again inverts its input causing its output to track the input of the NAND gate 90. Thus, the positive signal appearing at the data input terminal 68' results in a clock pulse to the counter 92 and enables the astable multivibrator 93. The counter 92 advances its state on the leading edge of signals applied to its clock input terminal. While the astable multivibrator 93 remains enabled, during a pulse appearing at the data input terminal 68', its output is applied to the clock impulse input terminal of counter 94 causing the counter 94 to advance its state in response to each pulse from the astable multivibrator 93. If the duration of the signal appearing at the data input terminal 68' is sufficient for the counter 94 to advance its state to the pin connected to the junction 97, the junction 97 will go HIGH causing the latches 100 and 101 to be set and apply at their outputs the inputs resulting from the logic circuitry composed of the NOR gates 102-108, NAND gates 109-112 and line 113. The signal appearing at junction 97 will trigger the monostable multivibrator 98 on its trailing edge causing the counter 92 to be reset or initialized to zero count. Subsequent signals appearing at the clock input terminal of counter 92 will again cause it to advance its state with the logic circuitry connected to its output terminals applying preselected electrode combinations to the inputs of the latches 100 and 101 in accordance with the state of the counter 92. Astable multivibrator 93, counter 94 and monostable multivibrator 98 form a digital pulse width discriminator the purpose of which is to determine the presence of the initial or first pulse in each train of data pulses forming a control signal, as will be explained more fully below.

Assuming now a control signal formed of a first pulse signal established by the monostable multivibrator 28 and successive pulse signals whose number is established by the counter 44. The first pulse signal will gate the astable multivibrator 93 on and release the reset of counter 94. Thus, the counter 94 will advance its count in response to clock signals from astable multivibrator 93. The duration of the pulse from the monostable multivibrator 28 is selected such that the astable multivibrator 93 will produce at least as many clock pulses to the counter 94 as are required to provide a pulse at the pin connected to the junction 97 while the successive control signal pulses will produce insufficient clock pulses to the counter 94 to cause the junction 97 to go HIGH. Thus, on the initial pulse signal of a control signal, the latches 100 and 101 are set, and the counter 92 reset, with successive pulses in the control signal each clocking the counter 92 and causing it to advance its state. Through the operation of the logic circuitry formed of NOR gates 102-108, NAND gates 109-112 and line 113, a predetermined output electrode configuration is established in predetermined correspondence with the count in the counter 92 with that output configuration being applied to the input of the latches 100 and 101. Each subsequent control signal will result in a setting of the latches 100 and 101 to apply at their outputs that preselected output electrode configuration that existed at the output of the logic circuitry immediately prior to the appearance of a pulse at the junction 97. The next stimulus signal will then be gated by the transmission gates 115 and 116 to the selected electrodes in accordance with the outputs of the latches 100 and 101.

From the above, it can be seen that the stimulator of the present invention will provide preselected output electrode combinations or configurations for each stimulus pulse, with the electrode combination being established separately for each stimulus signal. The electrodes A through G may be variously positioned around a nerve with different combinations explored until the optimal combination is established. If necessary, the electrode combinations can be altered by merely repositioning the selector arm 46 with regard to the pins of the counter 44. Alternatively, the selector 46 may be automatically moved to be in electrical communication with different pins to provide a sequential stimulation of various biological systems through appropriately placed electrodes A through G. Of course, the logic may be altered to provide different electrode combinations for the various states of the counter 92. With the illustrated logic, a high appearing at the various pins the counter 92 will result in an electrode selection as follows:

| Pin Number | Electrode Selection |
| --- | --- |
| 2 | A+, B− |
| 4 | B−, C+ |
| 7 | A+, C− |
| 10 | D+, E− |
| 1 | F+, G− |
| 5 | A+, B−, D+, E− |
| 6 | C+, B−, F+, G− |
| 9 | D+, E−, F+, G− |
| 11 | A+, B−, C+, D+, E−, F+, G− |

In addition, it has been found advantageous to operate the transmitter and receiver of FIGS. 1 and 2 with the following values or part designations:

| NAND gates | CD 4011 |
| --- | --- |
| Counter | CD 4017 |

AND gate 41 may be composed of a NAND gate with its output inverted by another NAND gate.

RECEIVER

| Inductances | Microhenrys |
| --- | --- |
| 55 | 20 |
| 56 | 10 |
| 58 | 3.3 |
| 59 | 6.8 |

| Resistances | Ohms |
| --- | --- |
| 66 | 10K |
| 67 | 100K |
| 73 | 470K |
| 76 | 680K |
| 83 | 3.3K |
| 87 | 2.2K |

| Capacitances | —— farads |
| --- | --- |
| 57 | 3900 pico |
| 60 | 620 pico |
| 61 | 470 pico |
| 69 | 120 pico |
| 72 | 4.7 micro |
| 77, 85 | 2.2 micro |
| 99 | 1000 pico |

OR gates 102, 103, 105, 106, 107, 108  CD 4001
OR gate 104  CD 4025
NAND gates  CD 4011
Counters 92, 94  CD 4017
Latches 100, 101  CD 4042
Transmission gates 115, 116  AD 7510

To assure a biphasic operation, and because the characteristics of the designated transmission gates 115 and 116 prevent their transmission of signals beyond the range of their power inputs, the negative voltage source appearing at terminal 75 is applied to the transmission gates 115 and 116 at the terminal 75'. This may be eliminated while maintaining a biphasic stimulation by providing each of the electrodes A through G with their own output capacitors, in known manner. Also, the connection of the junction 80 to the terminal 70 via diode 88 is intended to prevent the stimulus signals from exceeding the level of the voltage established at the point 70 to lessen the likelihood of excessive currents through the designated circuit elements, for reasons well known to those familiar with the art.

Many modifications and variations of the present invention are possible in light of the above teaching, for example, the illustrated logic circuitry may be altered to provide differing electrode combinations for each state of the counter 92, without departing from the scope of the present invention. Also, the number of electrodes may be altered without departing from the scope of the present invention. It is therefore to be understood that the invention may be practiced otherwise than as specifically described.

What is claimed is:

1. In an electrical stimulation system for selectively stimulating portions of the body of the type having external means for transmitting stimulus signals and control signals, implantable means for receiving said transmitted signals, a plurality of output means adapted to apply said stimulus signals to the body and means interconnecting said receiving means and said output means and responsive to said control signals for routing said stimulus signals to said output means, the improvement wherein: said output means are adapted for combination in a plurality of preselected configurations: said transmitting means includes means for alterably preselecting a predetermined characteristic of each control signal, said predetermined characteristic manifesting a desired one of said output means configurations; and said routing means comprises means for selectively routing said stimulus signals to the desired output means configuration in accordance with the predetermined characteristic of said control signals.

2. The system of claim 1 wherein each control signal comprises at least one pulse signal, said predetermined characteristic being the number of pulse signals within each control signal.

3. The system of claim 2 wherein said routing means comprises:
counter means for advancing state in response to said pulse signals; and
means for applying each stimulus signal across a preselected output means combination in predetermined correspondence with the state of said counter means following a different one of said control signals.

4. The system of claim 3 wherein said counter means is advanced from a predetermined state during each control signal.

5. The system of claim 4 wherein said stimulus signal applying means comprises:
means for gating said stimulus signals to said output means; and
means selectively enabling said gating means for establishing said preselected output means combination.

6. The system of claim 5 wherein said enabling means comprises:
decoder means for providing preselected gating means enable signal combinations in accordance with the count in said counter means; and
means interconnecting said decoder means and said gating means for applying said enable signals to said gating means.

7. The system of claim 6 wherein said enable signal applying means comprises means for applying a gating means enable signal combination to said gating means during a control signal and in predetermined correspondence with the number of pulse signals in the immediately previous control signal.

8. The system of claim 6 wherein said enable signal applying means comprises means for applying a gating means enable signal combination to said gating means in predetermined correspondence with the number of pulse signals in one control signal and on the occurrence of the next successive control signal, while maintaining the applied gating means enable signal combination until the occurrence of the second successive control signal.

9. The system of claim 8 wherein said routing means comprises:
counter means for advancing its state in response to said pulse signals; and
means for applying each stimulus signal across a preselected output means combination in predetermined correspondence with the state of said counter means following a different one of said control signals.

10. The system of claim 9 further comprising means for resetting said counter means in response to said first pulse signals.

11. The system of claim 16 wherein said stimulus signal applying means comprises:
means for gating said stimulus signals to said output means; and
means selectively enabling said gating means for establishing said preselected output means combination.

12. The system of claim 11 wherein said enabling means comprises:
decoder means for providing preselected gating means enable signal combinations in accordance with the count in said counter means; and
means interconnecting said decoder means and said gating means for applying said enable signals to said gating means.

13. The system of claim 12 wherein said enable signal applying means comprises means responsive to a control signal first pulse signal for applying a gating means enable signal combination to said gating means in predetermined correspondence with the number of pulse signals in the previous control signal.

14. The system of claim 13 wherein said first and successive pulse signals are discriminable by pulse duration.

15. The system of claim 2 wherein said means for alterably preselecting the number of pulse signals within each control signal comprises means for generating a first pulse signal and an alterable number of successive pulse signals discriminable from said first impulse signal.

16. The system of claim 1 wherein said means for alterably preselecting a predetermined characteristic of each control signal comprises means for generating a first pulse signal of predetermined duration and an alterable number of successive pulse signals of shorter duration, said routing means comprising counter means for advancing its state from a predetermined state in response to said pulse signals.

17. The system of claim 16 further comprising:
means responsive to said pulse signals for detecting said first pulse signal; and
means responsive to said detecting means for resetting said counter means.

18. The system of claim 17 wherein said detecting means comprises:
means for producing a train of pulses at a preselected frequency during said impulse signals;
second counter means for advancing its state in response to each pulse in said pulse train; and
means for producing a routing means counter means reset signal when the state of said second counter means advances to a preselected state.

19. The system of claim 18 further comprising means for resetting said second counter means after each impulse signal.

20. The system of claim 16 further comprising:
means for gating said stimulus signals to said output means;
decoder means for providing preselected gating means enable signal combinations in accordance with the state of said counter means; and
means responsive to said first pulse signals for applying a gating means enable signal combination to said gating means in accordance with the state of said counter means immediately following said first pulse signals.

21. The system of claim 20 wherein said applying means comprises latch means for maintaining said enable signal combinations during the interval between successive first pulse signals.

22. The system of claim 21 further comprising:
means for producing a train of pulses at a preselected frequency during said pulse signals;
second counter means for advancing its state in response to each pulse in said pulse train;
means for setting said latch means when said second counter means advances to a preselected state; and
means for resetting said routing means counter means a predetermined time after second counter means advances to said preselected state.

23. The system of claim 22 further comprising means for resetting said second counter means after each pulse signal.

24. The system of claim 1 wherein at least two of said output means configurations include a common output means.

25. A body implantable stimulator which comprises:
means for receiving transmitted signals of first and second frequencies;
a plurality of output means adapted for connection to the body in a plurality of preselected configurations;
means for detecting a predetermined characteristic of the first frequency signals occurring between consecutive second frequency signals, said predetermined characteristic manifesting a desired one of said output means configurations; and
means for selectively applying each second frequency signal to the desired output means configuration in predetermined correspondence with the predetermined characteristic of the first frequency signals detected between different, consecutive second frequency signals.

26. The stimulator of claim 25 wherein said detecting means comprises counter means for altering its state from a predetermined state in accordance with the predetermined characteristic of each first frequency signal.

27. The stimulator of claim 26 further comprising means for resetting said counter means between consecutive second frequency signals.

28. The stimulator of claim 27 wherein said applying means comprises:
means for gating said second frequency signals to said output means;
decoder means for providing preselected gating means enable signal combinations in accordance with the state of said counter means; and
means interconnecting said gating means and said decoder means for maintaining a gating means enable signal combination after resetting of said counter means.

29. The stimulator of claim 28 wherein said first frequency signal predetermined characteristic is the number of first frequency signals occurring between consecutive second frequency signals.

30. The stimulator of claim 29 further comprising means responsive to the initial first frequency signal following each frequency signal for resetting said counter means.

31. The stimulator of claim 30 wherein said maintaining means comprises latch means, said stimulator further comprising:
means providing a control signal in response to the initial first frequency signal following each second frequency signal;
means applying said control signal to said latch means for setting said latch means; and
means responsive to said control signal for resetting said counter means a predetermined time following the appearance of said control signal.

32. The stimulator of claim 26 further comprising means responsive to the initial first frequency signal following each second frequency signal for resetting said counter means.

33. The stimulator of claim 32 wherein said applying means comprises:
means for gating said second frequency signals to said output means;
decoder means for providing preselected gating means enable signal combinations in accordance with the state of said counter means; and
means interconnecting said gating means and said decoder means for maintaining a gating means enable signal combination after resetting of said counter means.

34. The stimulator of claim 25 wherein at least two of said output means configurations include a common output means.

* * * * *

UNITED STATES PATENT AND TRADEMARK OFFICE
CERTIFICATE OF CORRECTION

PATENT NO. : 4,019,518
DATED : April 26, 1977
INVENTOR(S) : Donald D. Maurer, and Paul D. Sorenson It is certified that error appears in the above-identified patent and that said Letters Patent are hereby corrected as shown below:

Cover Page, in the ABSTRACT, line 4 of the second column, "devies" should be --devices--.

Column 7, line 1, "group" should be --ground--.

Column 7, line 17 should be the beginning of a new paragraph.

Column 10, line 1 of Claim 11, "16" should be --10--.

Column 12, line 3 of Claim 30, after "each", insert --second--.

Signed and Sealed this sixteenth Day of August 1977

[SEAL]

Attest:

RUTH C. MASON
Attesting Officer

C. MARSHALL DANN
Commissioner of Patents and Trademarks

REEXAMINATION CERTIFICATE (581st)

United States Patent [19]

Maurer et al.

[11] B1 4,019,518

[45] Certificate Issued  Oct. 14, 1986

[54] ELECTRICAL STIMULATION SYSTEM

[75] Inventors: Donald D. Maurer, Anoka; Paul D. Sorenson, Blaine, both of Minn.

[73] Assignee: Medtronic, Inc., Minneapolis, Minn.

Reexamination Request:
No. 90/000,376, May 9, 1983

Reexamination Certificate for:
Patent No.: 4,019,518
Issued: Apr. 26, 1977
Appl. No.: 603,434
Filed: Aug. 11, 1975

Certificate of Correction issued Aug. 16, 1977.

[51] Int. Cl.$^4$ ............................................. A61N 1/36
[52] U.S. Cl. ................................. 128/419 R; 128/783
[58] Field of Search ........ 128/419 C, 419 E, 419 PG, 128/419 R, 420 R, 421, 422, 423 R, 783

[56] References Cited

U.S. PATENT DOCUMENTS

| | | | |
|---|---|---|---|
| 2,708,744 | 5/1955 | Neiswinter | 340/164 |
| 2,812,509 | 11/1967 | Phelps | 340/147 |
| 2,996,704 | 8/1961 | Dimond et al. | 340/353 |
| 3,179,890 | 4/1965 | Warner | 325/326 |
| 3,261,920 | 7/1966 | Aaron | 179/15 |
| 3,326,207 | 6/1967 | Egan | 128/2.06 |
| 3,510,777 | 5/1970 | Gordon | 325/55 |
| 3,510,780 | 5/1970 | Buehrle | 325/321 |
| 3,511,923 | 5/1970 | Ameau et al. | 178/4.1 |
| 3,611,297 | 10/1971 | Kramer et al. | 340/171 R |
| 3,646,940 | 3/1972 | Timm et al. | 128/421 |
| 3,699,970 | 10/1972 | Brindley et al. | 128/419 R |
| 3,727,616 | 4/1973 | Lenzkes | 128/422 |
| 3,727,616 | 4/1973 | Lenzkes | 128/422 |
| 3,805,796 | 4/1974 | Terry, Jr. et al. | 128/419 P |
| 3,805,796 | 4/1974 | Terry, Jr. et al. | 128/419 |
| 3,822,708 | 7/1974 | Zilber | 128/419 R |
| 3,825,015 | 7/1974 | Berkovits | 128/404 |
| 3,831,039 | 8/1974 | Henschel | 307/234 |
| 3,833,005 | 9/1974 | Wingrove | 128/419 P |
| 3,833,005 | 9/1974 | Wingrove | 128/419 |
| 3,833,005 | 9/1974 | Wingrove | 128/419 P |
| 3,858,116 | 12/1974 | Friedl et al. | 325/37 |
| 3,888,261 | 6/1975 | Maurer | 128/420 |
| 3,944,982 | 3/1976 | Mogi et al. | 340/171 R |

OTHER PUBLICATIONS

Warner et al., "IEEE Transactions On Biomedical Engineering" vol. 15, No. 2, Apr. 19.
A Remote Control Brain Telestimulator With Solar Cell Power Supply, Harold Warner, Member, IEEE, Bryan W. Robinson, H. E. Rosvold, Lawrence D. Wechsler, Member, IEEE, and J. J. Zampini, Member, IEEE,-IEEE Transactions On Bio-Medical Engineering, vol. BME-15, No. 2, Apr. 1968-pp. 94–101.
An Implantable Multi-Channel Biotelemetry System, J. Donald Pauley, Martin Reite, and Stephen D. Walker,-Electroencephalography and Clinical Neurophysiology, 1974, 37: 153–160.

*Primary Examiner*—William E. Kamm

[57] ABSTRACT

An electrical stimulation system for selectively stimulating portions of the body. The system includes an external device for alternately transmitting stimulus signals and control signals to an implantable receiver. The receiver includes a plurality of output devices adapted to apply the stimulus signals to the body and circuitry for routing the stimulus signal to the output devices under the control of the control signals. In a preferred embodiment, the control signals are formed of an alterably preselected number of pulse signals with the routing circuitry routing each of the stimulus signals to the output devices in predetermined correspondance with the number of pulse signals within a different one of the control signals. The system of the present invention may be employed to sequentially stimulate several stimulation sites, with the stimulation sites being selected to combat the same or different body disfunctions. Alternatively, the system of the present invention may be employed to repetitively stimulate the same stimulation sites while allowing an alteration in the stimulation sites to combat nerve fatigue or to provide a more effective electrode configuration, for example.

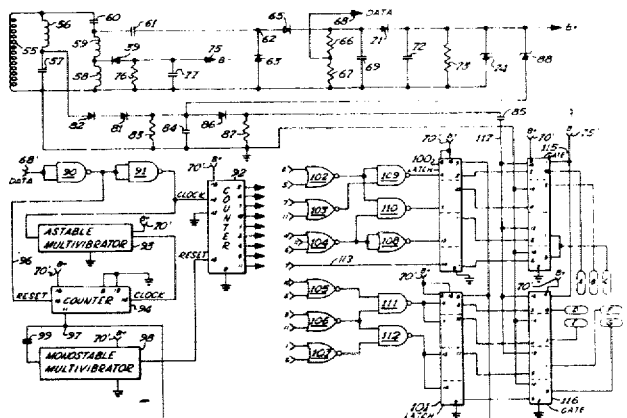

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-34 are cancelled.

* * * * *